United States Patent [19]

Langer et al.

[11] Patent Number: 4,724,394

[45] Date of Patent: Feb. 9, 1988

[54] GAS DETECTION BY ION MOBILITY SEGREGATION

[75] Inventors: Scott R. Langer, Westminster; William D. Bowers, Newport Beach; Michael F. Steele, Fountain Valley; Raymond L. Chuan, Huntington Beach, all of Calif.

[73] Assignee: Brunswick Corporation, Skokie, Ill.

[21] Appl. No.: 786,666

[22] Filed: Oct. 11, 1985

[51] Int. Cl.[4] .............................................. G01N 27/62
[52] U.S. Cl. ...................................... 324/464; 73/23; 422/83
[58] Field of Search ........................ 324/464; 73/23; 204/165; 422/83, 90, 98; 436/153

[56] References Cited

U.S. PATENT DOCUMENTS 4,114,088  9/1978  Laws ................................ 324/464

4,456,883  6/1984  Bullis et al. ..................... 324/464

Primary Examiner—Reinhard J. Eisenzopf
Assistant Examiner—Robert W. Mueller
Attorney, Agent, or Firm—Lyon & Lyon

[57] ABSTRACT

A device for gas detection through ion mobility segregation by mobility ranges includes a flow tube through which a sample of atmospheric air with possible contaminant gases flow. Ions formed of gases in the air and the possible contaminant gases are segregated by ion mobility range in either a first, second or subsequent electric field positioned along the flow tube. The ions are collected on an anode or cathode of each electric field. The ions of the gases striking an anode or cathode by charge transfer induce a detection current, the measure of which indicates the presence of gases of interest. A method for detecting a gas by ion mobility segregation is also described.

28 Claims, 4 Drawing Figures

GAS DETECTION BY ION MOBILITY SEGREGATION

BACKGROUND OF THE INVENTION

The field of the present invention is gas detection and particularly gas detection determined by ion mobility range segregation.

Historically, gas detection utilizing ion molecule reactions and subsequent detection of the resulting analyte ions by their differing ion mobilities have been accomplished by two different detection methods. In each method, the reactant ions, formed by a variety of techniques, undergo ion molecule reactions with the sample molecules whereby stable positive or negative product ions are produced. These detection methods for the product ions are:

(1) Plasma chromatography. Here, ion identification is achieved by selective ion gating followed by statistical analysis of the time required for the ions to reach a collector. Since different ions have different mobilities in the presence of an electric field, the collection time can be used for ion identification.

(2) Detection by diffusion. Here, ions are contained in a constant flow stream, and travel through a complex geometric labyrinth in which they are separated by radial diffusion and subsequent neutralization before reaching the collector. The larger product ions which are able to reach the collector before neutralization are detected.

These prior methods are limited in practicability in that their functional use requires complex geometries for each type of ion requiring detection or complex time base data collection techniques and analysis for mobility identification.

SUMMARY OF THE INVENTION

The present invention is directed to an advancement in commercial gas detection techniques wherein ion segregation based on discrete ion mobility ranges reduces system complexity to a constant flow stream through controlled electric fields.

Theoretically, this technique is based on the phenomenon that electric fields can be used to influence the motion of mobile ions which have been formed by any standard ionization process. In the case of this invention, the electric fields are formed by applying a voltage potential to electrodes spaced along a flow stream. The forces acting on the ions in said flow stream are then of two origins: flow forces and field forces. Proper operation of the device is dependent upon controlling flows and fields so that the interaction of flow and field forces yields the desired ion motion. The flow forces are primarily directed axially along the tube and are constant in the direction of the flow. The field forces are complex and their effect on the ions vary in magnitude and direction as the ions travel through the field. The positive pole of the field will attract a negatively-charged ion and repel a positively-charged ion and the opposite is true for the negative pole of the field. The interaction of these forces on the ions is evidenced by a measurement of the current generated by ion/electrode charge transfer as the ions collide with the electrodes. Positive ion collision generates a positive current, while negative ion collision generates a negative current. Thus, the entrained ion charges are collected by the appropriately charged pole of the electric field, wherein the induced current is measured.

The present invention provides segregation of the ion stream into discrete ranges of ionic mobility wherein said discrete mobility range charge transfers can be measured at a specific field electrode. Normally, measurement of only one particular polarity and mobility range is made at one time. However, several collection stages can be used in a series arrangement to collect ions in either polarity in mobility ranges from high to low. The device would then behave as a series of bandpass filters with each stage collecting charge transfers for a particular range of mobilities.

DETAILED DESCRIPTION OF THE PREFERRED EMBODIMENT

Figure 1:
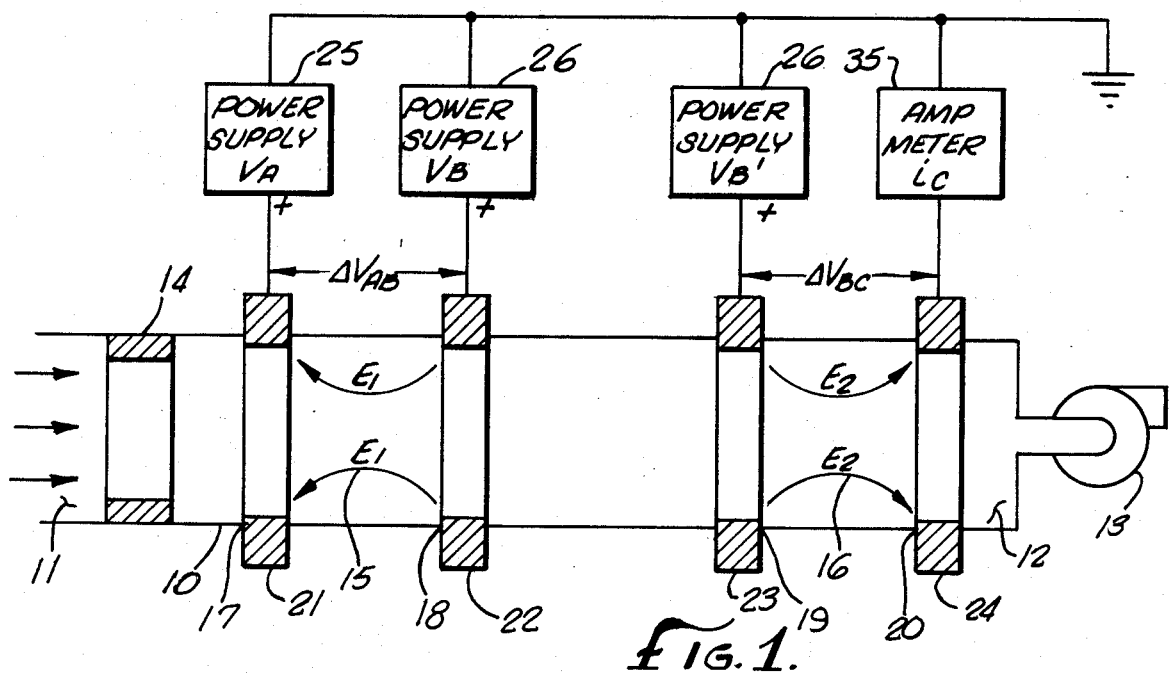
FIG. 1 is a schematic view of a device of the invention, configured to detect a gas forming primarily positively-charged ions of a specific mobility species.

Apparatus is shown in FIG. 1, which may be used to determine the presence of a contaminant gas by segregating ions into mobility ranges where the contaminant gas forms positively-charged ions by chemical reaction with ionized atmospheric air produced reactant ions. The apparatus shown in FIG. 2 performs the same function for a contaminant gas forming negatively-charged ions.

The apparatus or device for gas detection by ion mobility segregation shown in FIG. 1 includes a flow tube 10. The flow tube 10 has a first open end or inlet 11 and a second end or outlet 12 connected to a blower 13. The blower 13 pulls an atmospheric air sample through the flow tube 10 at a fixed average flow stream velocity. A pump could just as well be used to push an air sample through the flow tube 10.

Adjacent the inlet 11 a radiation source 14 ionizes gases within the atmospheric air stream. The gases in the air stream are ionized (electrically charged) to produce reactant ions, primarily $(H_2O)_nH^+$ and $(H_2O)_mO_2^-$. The values of n and m depend on the amount or concentration of water vapor in the atmosphere air stream. Accordingly, the humidity can be controlled to establish different mobility ranges. Atmospheric air is a mixture of known gases and may also contain other contaminating gases which can react with the reactant ions to form stable product ions. These stable product ions of the contaminant gas are the ions of interest for identification and detection.

Referring to FIG. 1, a field $E_1$ or first electric field 15 and a field $E_2$ or second electric field 16 are formed along the flow tube 10. These fields 15 and 16 are formed generally axially but may be of any other complex geometry or direction. The first electric field 15 is formed between a first position 17 spaced from a second position 18 to segregate and collect ions from the gas stream within the flow tube 10 which have a first mobility range.

The second electric field 16 is positioned downstream of the first electric field 15 and is formed between a third position 19 spaced from a fourth position 20 to segregate and collect ions from the gas mixture which have a second mobility range. In FIG. 1, the second position 18 of the first electric field 15 and the third position 19 of the second electric field 16 are spaced from each other. The second position 18 may also be about the same position as the third position 19 or may be the same position.

In the preferred embodiment, the first electric field 15 includes a first electrode 21 positioned along or annularly about the flow tube 10 at the first position 17 and a second electrode 22 also positioned along or annularly about the flow tube 10 at the second position 18 and spaced from the first electrode 21. The second electric field 16 includes a third electrode 23 positioned along or annularly about the flow tube 10 at the third position 19 and a fourth electrode 24 positioned along or annularly about the flow tube 10 at the fourth position 20. In the preferred embodiment, the second electrode 22 and the third electrode 23 are separated by some distance along the flow tube 10 as shown in FIG. 1. However, electrode 22 and electrode 23 may be combined into a single electrode. Additionally, in the case where the space is large between electrodes 22 and 23 as compared to the space between the electrode sets 21 and 22, and 23 and 24, the direction of field $E_2$ for the electric field 16 is unimportant.

A first power supply 25 provides a voltage ($V_A$) to the first electrode 21 and a second power supply 26 provides a voltage ($V_B$) to the second electrode 22. This provides a field $E_1$ or first electric field 15 along the flow tube 10 having a differential voltage $\Delta V_{AB}$ between the first electrode 21 and the second electrode 22. A third power supply 27 also provides a voltage ($V_{B'}$) to the third electrode 23. The fourth electrode 24 is maintained at or about ground potential. The field $E_2$ or second electric field 16, has a voltage $\Delta V_{B'C}$ between the third electrode 23 and fourth electrode 24. In the preferred embodiment of FIG. 1 the voltage ($V_B$) is greater than the voltage ($V_A$), the voltage ($V_{B'}$) is greater than the voltage ($V_C$), and the voltage difference $\Delta V_{B'}$ is greater than the voltage difference $\Delta V_{AB}$. The system may also be configured such that $V_B = V_{B'}$ or further that power supplies 26 and 27 are the same power supply.

To detect the presence of a contaminant gas G of interest which forms primarily positive product ions from a gas phase ion molecule reaction with the reactant ions present in ionized atmospheric air, the device of FIG. 1 is used. The first electric field 15 and the second electric field 16 are generated by applying specific voltage potentials to the four electrodes 21 through 24. It is the polarity and strength of these electric fields which perform the segregation or separation and collection of the reactant and product ions contained in the flow tube. The first electric field 15 separates and collects those ions having higher mobility than the product ions of gas of interest G. The positive ions (charges) are collected on electrode 21 and the negative ions (charges) are collected on electrode 22 for these ions having a mobility greater than the mobility range of the gas G of interest. The ions of the gas G of interest continue to travel down the tube and are separated and collected in the second electric field 16. The product ions which have a mobility range less than the mobility range of the reactant ions collected in the first stage of the apparatus controlled by the electric field 15, pass through the first stage and flow down the flow tube 11 entering the second stage electric field 16. In the second stage electric field 16 the negative product ions (charges) are collected on electrode 23 and the positive product ions (charges) are collected on electrode 24. The collection of positive product ion charges on electrode 24 induces a current which is measured by an ampmeter 33 which is connected to electrode 24. An increase in current $i_C$ indicates the presence of a gas G of interest. In the same manner in which the strength of electric field 15 is set to separate and collect those ions within the reactant ion mobility range the strength of electric field 16 can be set to collect only those ions of a specific product ion mobility range. It then follows that many sets of electric fields can be used in series with each successive electric field collecting a family of ions of lower mobility range than those separated and collected in the preceding electric field (stage). Any electrode in this arrangement can be attached to an ampmeter to detect a presence of ions of the specific mobility range being collected at any electrode.

Figure 3A:
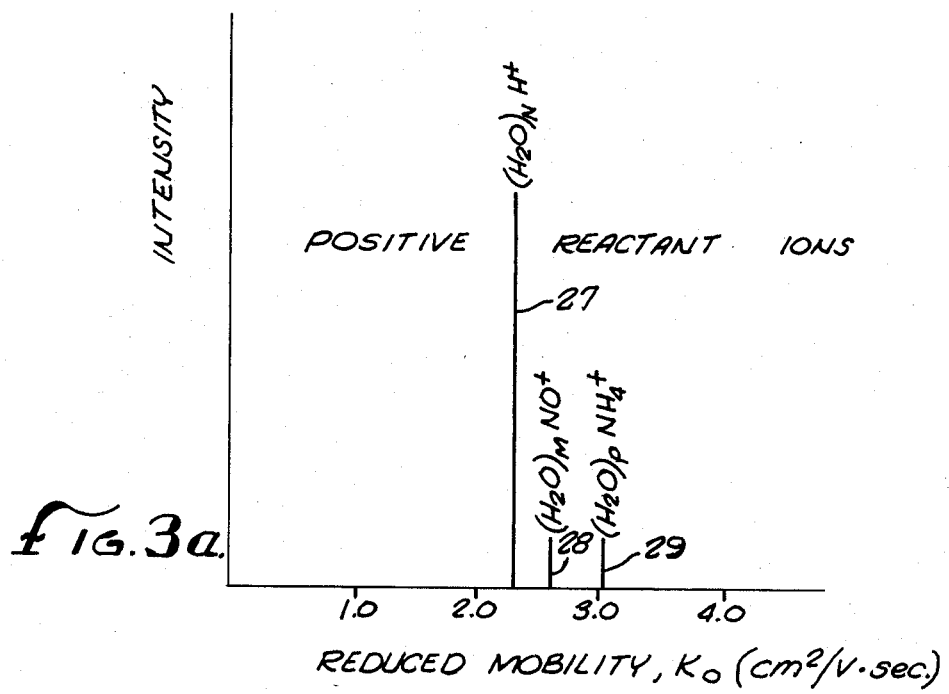
FIGS. 3a and 3b illustrate the intensity versus mobility of clean air and of clean air with a gas sample (G).
Figure 3B:
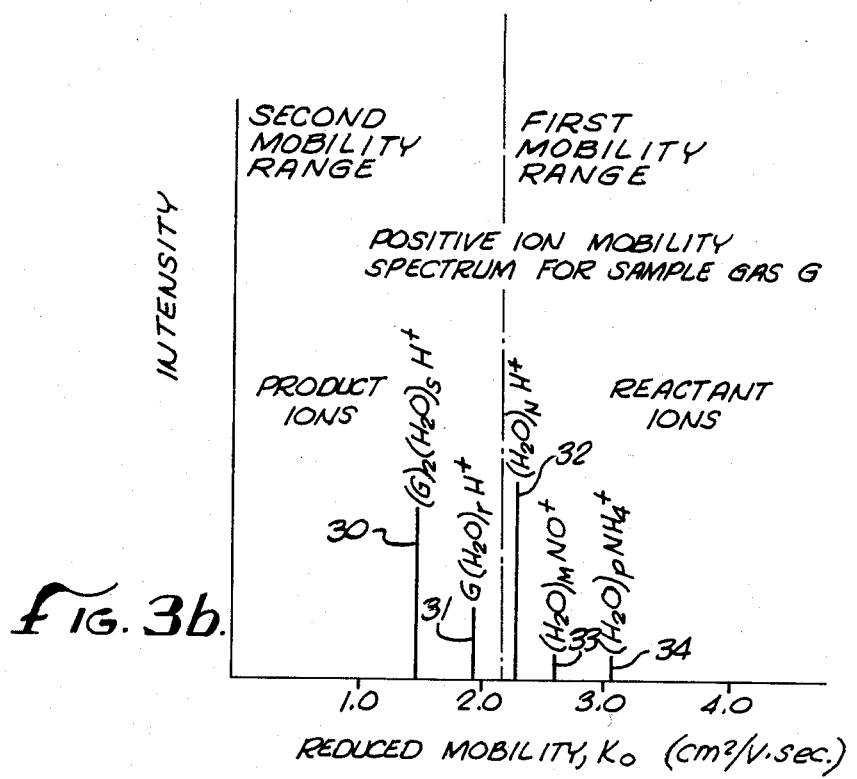

FIGS. 3a and 3b show the change in mobility when a contaminant gas G (in this case, dimethyl methyl phosphonate or DMMP) is added to clean air. FIG. 3a shows the intensity vs. mobility for the reactant ions produced from clean air. FIG. 3b shows the intensity vs. mobility of ions produced when DMMP is added. Note the formation of product ions DMMP $(H_2O)_r H^+$ and $(DMMP)_2 (H_2O)_s H+$ where none was indicated with clean air. Also note the reduction in intensity of the reactant ions. The first electric field 15 would be used to collect all the reactant ions. This would allow the product ions to be collected by the electrodes forming the second electric field 16 where an increase in current (i) would indicate the presence of the contaminant gas DMMP.

In the device shown in FIG. 1, the diameter of the flow tube 10 is about one-quarter inch, the spacing between the first and second electrode rings 21 and 22 is about one-quarter inch and the spacing between the third and fourth electrode rings 23 and 24 is about one-quarter inch. The voltage $V_A$ is 200 volts, the voltage $V_B$ equals the voltage $V_{B'}$ and is 500 volts and the voltage $V_C$ at electrode 24 is about ground. This provides a $\Delta V_{AB}$ of 300 volts and a $\Delta V_{B'C}$ of 500 volts. The flow stream velocity is about 1.2 meters per second with a flow volume of 1.3 liters per minute.

Figure 2:
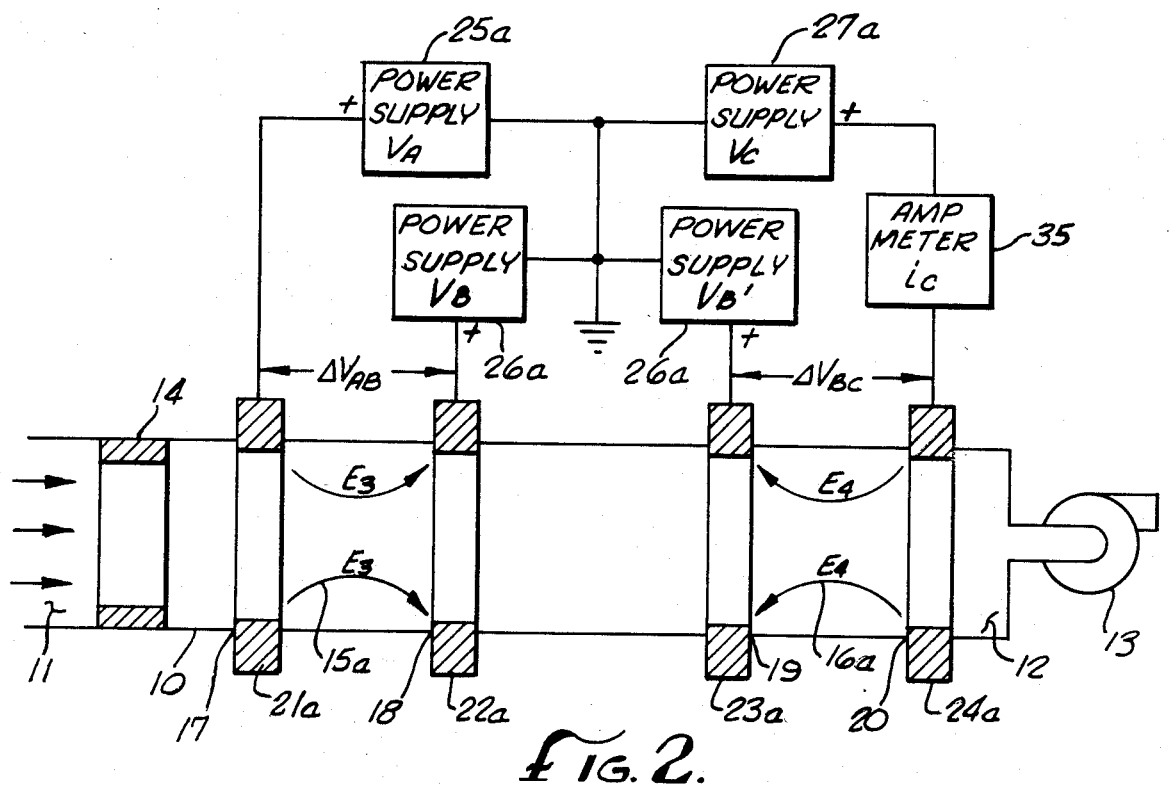
FIG. 2 is a schematic view of a device similar to FIG. 1 configured to detect a gas forming primarily negatively-charged ions of a specific mobility species.

The apparatus shown in FIG. 2 includes identical or substantially equivalent components as that of FIG. 1. Identical components are identified by the same reference numbers and equivalent components are identified by reference numbers having the subscript (a). The field $E_4$ is functionally equivalent to the field $E_1$ except reversed to collect negatively-charged reactant ions and the field $E_4$ is functionally equivalent to the field $E_2$ except reversed to collect negatively charged product ions.

Thus, a device and method is described for segregating or separating and collecting ions of either polarity within specific ranges of ion mobility to determine the presence of a gas G of interest. While embodiments and applications of this invention have been shown and described, it would be apparent to those skilled in the art that many more modifications are possible without departing from the inventive concepts herein. The invention therefore, is not to be restricted except in the spirit of the appended claims.

What is claimed is:

1. A device for gas detection by ion mobility segregaton comprising
   a flow tube having a closed cross-section providing a flow path for a stream of a gas mixture containing ions formed from gases therein, and
   an electric field positioned along said flow tube generally parallel to said flow path and formed between two spaced positions, one of said two spaced positions being a cathode and the other of said spaced positions being an anode, said electric field having a field strength to separate and collect iions of a specific mobility range on one of said anode and cathode.

2. The device of claim 1 wherein said electric field comprises
   a first electric field formed along said flow tube between a first and second spaced position to segregate ions from said gas which have a first mobility range, and
   a second electric field downstream of said first electric field formed along said flow tube between a third and fourth spaced position to segregate ions from said gas which have a second mobility range which has lower mobility than said first mobility range.

3. The device of claim 2 wherein said second position of said first electric field and said third position of said second electric field are the same position.

4. The device of claim 3 further comprising a second electrode disposed at said second position as a cathode of said first electric field and a third electrode disposed at said third position as an anode of said second electric field.

5. The device of claim 3 further comprising a second electrode disposed at said second position as an anode of said first electric field and a third electrode disposed at said third position as an anode of said second electric field.

6. The device of claim 2 wherein said first mobility range includes reactant ions from gases within atmospheric air.

7. The device of claim 2 wherein said second mobility range includes product ions of a gas G of interest having a known ion mobility range.

8. The device of claim 2 wherein said first electric field segregates a gas having said first mobility range and said second electric field segregates a gas having said second mobility range.

9. The device of claim 2 further including a detection unit to advise of the segregation of ions of at least one of said mobility ranges.

10. The device of claim 2 further comprising a radiation source disposed adjacent to said flow tube and upstream of said first electric field.

11. A device for ion mobility segregation comprising a first electric field having a first cathode spaced from a first anode along a gas stream flow path to separate and collect ions from said gas stream which have a first mobility range,
    a second electric field positioned downstream from said first electric field having a second cathode spaced from a second anode along said gas stream flow path to separate and collect ions from said gas stream which have a second mobility range, and
    a detection unit to indicate a segregation of ions in said second electric field.

12. The device of claim 11 wherein said first electric field comprises a first electrode ring positioned annularly about said gas flow path and a second electrode ring positioned annularly about said gas flow path and spaced from said first electrode ring and said second electric field comprises a third electrode ring positioned annularly about said gas flow path and a fourth electrode ring positioned annularly about said gas flow path and spaced from said third electrode ring, said first electric field being generally axial between said first electrode ring and said second electrode ring and said second electric field being generally axial between said third electrode ring and said fourth electrode ring.

13. The device of claim 12 wherein said second electrode ring and said third electrode ring are a single combined electrode ring.

14. The device of claim 13 wherein said combined electrode ring is at a positive voltage.

15. The device of claim 13 wherein said combined electrode ring is at a negative voltage.

16. The device of claim 12 wherein said first electric field separates and collects at least one of the positive ions and negative ions within the reactant ion or said first mobility range on the first or second electrode ring.

17. The device of claim 12 wherein said second electric field separates and collects at least one of the positive ions and negative ions within the product ion or said second mobility range on the third or fourth electrode ring.

18. The device of claim 12 wherein said first electric field separates and collects at least one of the positive ions and negative ions within the reactant ion or said first mobility range and the said second electric field separates and collects at least one of the positive ions and/or negative ions within the product ion or said second mobility range.

19. A method of collecting ions within ion mobility ranges comprising
    flowing a stream of a gas mixture having ions representative of gases therein through an electric field positioned along said stream, said electric field having a specified field intensity,
    collecting a first group of ions at one end of said electric field and,
    measuring the first group of ions collected in said electric field to detect the representative gas.

20. A method for collecting ions by ion mobility range comprising
    forming ions of gases in a flow stream of a gas mixture, and
    collecting a group of ions having a known range of mobility at one end of an electric field extending axially along said flow stream.

21. The method defined in claim 20 further comprising measuring an electric current from said collected ions to indicate the presence of a gas of interest in said gas mixture.

22. The method defined in claim 21 wherein said collected ions are positive ions collected on a cathode of said electric field.

23. The method defined in claim 21 wherein said collected ions are negative ions collected on an anode of said electric field.

24. A method for detecting a gas by ion mobility segregation comprising
    forming ions of gases in a flow stream of a gas mixture,
    establishing a first and second electric field in series along said flow stream, collecting in said first electric field a first group of ions having a first mobility range, and collecting in said second electric field a second group of ions having a second mobility range of a gas G of interest.

25. The method defined in claim 24 further comprising the step of irradiating the flow stream to form ions within said flow stream prior to or within the region of said first electric field.

26. The method defined in claim 24 further comprising measuring an electric current from said collected ions to indicate the presence of a gas G of interest in said gas mixture.

27. The method defined in claim 24 further comprising establishing more than two said electric fields along said flow stream wherein a discrete specific mobility range can be separated and collected within each electric field.

28. The method defined in claim 27 further comprising measuring electric currents at each of said electric fields from said collected ions to indicate the presence of gases of interest within said specific mobility ranges.

* * * * *